United States Patent [19]
Zeller et al.

[11] Patent Number: 6,055,292
[45] Date of Patent: Apr. 25, 2000

[54] METHOD AND APPARATUS FOR PRODUCING X-RAY EXPOSURES OF BODY PARTS OF A HUMAN

[75] Inventors: Uwe Zeller, Neu-Anspach; Werner Günther, Bensheim; Ulrich Schulze-Ganzlin; Michael Döbert, both of Lorsch, all of Germany

[73] Assignee: Sirona Dental Systems GmbH & Co. KG, Bensheim, Germany

[21] Appl. No.: 09/024,776

[22] Filed: Feb. 17, 1998

[30] Foreign Application Priority Data

Feb. 17, 1997 [DE] Germany .......................... 197 06 102

[51] Int. Cl.[7] ...................................................... A61B 6/14
[52] U.S. Cl. ................................ 378/21; 378/39; 378/146
[58] Field of Search .................................. 378/21, 22, 23, 378/24, 38, 39, 40, 98.8, 146

[56] References Cited

U.S. PATENT DOCUMENTS

4,709,382  11/1987  Sones .......................................... 378/62
4,773,087   9/1988  Plewes ....................................... 378/146
4,847,881   7/1989  Heubeck .
5,511,106   4/1996  Doebert et al. .

*Primary Examiner*—David P. Porta
*Attorney, Agent, or Firm*—Hill & Simpson

[57] ABSTRACT

In a method and an apparatus for producing X-ray tomograms of the jaw and skull of a patient, a detector arrangement having at least one x-ray detector is provided. The radiation-sensitive area of the detector is a sub-area of the total detector area required for the subject exposure. The image exposure ensues in a number of chronologically separate sections in which, following a first sub-exposure, the detector arrangement is displaced along the longitudinal axis and/or the transverse axis of the detector surface and the diaphragm aperture of the primary diaphragm associated with the x-ray source is simultaneously correspondingly adapted so that the position of the x-ray beam is shifted so that it still strikes the detector appropriately after the detector is displaced.

19 Claims, 6 Drawing Sheets

METHOD AND APPARATUS FOR PRODUCING X-RAY EXPOSURES OF BODY PARTS OF A HUMAN

BACKGROUND OF THE INVENTION

1. Field of the Invention

The present invention is directed to a method and to an apparatus for producing X-ray exposures of body parts of a human, particularly X-ray tomograms of the jaw or skull of a patient, whereby a ray beam generated by a radiation source and limited by a diaphragm aperture of a primary diaphragm strikes a detector arrangement after penetrating through the exposure subject, the detector arrangement having at least one X-ray image-acquiring detector element.

2. Description of the Prior Art

Methods and apparatuses are employed in dental radiology with which it is possible to produce tomograms of a human, particularly of the region of the jaw. A particular application is the production of tomograms whose slice proceeds perpendicular to the mandibular arch. Such tomograms are called transversal sections. Compared to otherwise standard panorama tomograms, such transversal sections exhibit an especially small range of the depth of field. European Application 0 229 971 discloses an apparatus with which such tomograms are produced on an X-ray film.

European Application 0 632 994 discloses an apparatus for producing X-ray exposures digitally. To this end, a line detector camera with a detector that is implemented as a single-stage or multi-stage CCD sensor is provided. Dependent on whether a single-stage or multi-stage sensor is employed, the dimensions of the detector arrangement typically amount to 135 through 180 mm in the image height and approximately 6 mm in the image width. These dimensions take into account, first, the image acquisition size necessary for a good diagnosis and, second, an adequate depth of field when viewing the individual slices. It has been shown in practice that the diaphragm system and detector system must be matched such that the usable ray fan for transversal slices, i.e. for the aforementioned transversal sections, must exhibit a width of at least 20 mm in the detector plane in order to be able to achieve a range of approximately 1 through 3 mm for the depth of field. A detector arrangement on the order of the aforementioned size is comparatively expensive with current technology.

SUMMARY OF THE INVENTION

An object of the present invention is to provide a method and an apparatus with which it is possible to produce tomograms of the type described above with a smaller, more economical detector surface area.

A significantly smaller and thus more economic detector can be utilized in the exposure procedure that inventively ensues in a number of chronologically separated sections for which the detector or a detector arrangement composed of a number of detectors is arranged in different positions. It is especially economical when the detector employed exhibits the dimension of a detector of the type known as an intra-oral sensor, as is currently employed for intra-oral exposures, or when a complete intra-oral sensor of this type is utilized as the detector. Typically, such sensors have dimensions of about 30×20 mm. The sensor of the type already used per se for intra-oral exposures thus can also be employed for extra-oral exposures (dual use).

When a number of transversal tomograms are to be produced, it can be advantageous to implement the sub-exposures not only in the forward phase but also in the return phase of the rotary unit that carries the X-ray source and the detector arrangement. The overall exposure sequence thus can be significantly accelerated. Also for shortening the exposure sequence, it can be advantageous to undertake a detector displacement only when all transversal tomograms for one position, i.e. for one sub-exposure position of the detector arrangement, have been completed.

It can also be advantageous to provide a number of detectors and to arrange these spaced from each other. Such an arrangement with a number of detectors is still more economical than a detector arrangement having the initially described image acquisition size.

DESCRIPTION OF THE PREFERRED EMBODIMENTS

Figure 1:
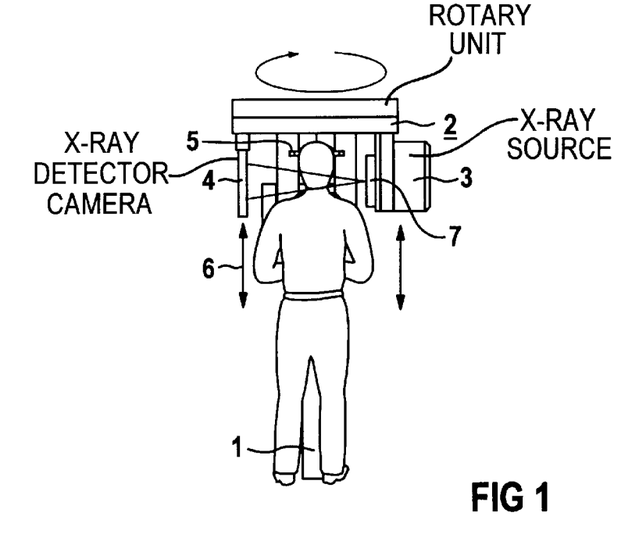
FIG. 1 shows dental X-ray diagnostics apparatus in a side view constructed and operated in accordance with the invention.

In a schematic illustration, FIG. 1 shows a dental X-ray diagnostic apparatus for producing panorama tomograms that, according to the invention, can also be utilized for the production of transversal sections. The apparatus contains a height-adjustable carrying column 1 at which a rotary unit 2 is held. The rotary unit 2 carries an X-ray source 3 and an X-ray detector camera 4 diametrically opposite. A head retainer and positioning arrangement 5 allows the patients head to be fixed in a defined position in a known way. The structure as well as adjustment possibilities of the rotary unit 2 and of the head retainer and positioning arrangement 5 are known and, for example, are disclosed in the initially cited European Application 0 632 994. The line camera 4 is composed of an oblong housing having a slot (not referenced in detail) at its side facing toward the radiation source 3. A detector arrangement 8 having one or more radiation-sensitive detectors, for example in the form of CCD sensors, is located in the inside of the camera 4 behind the slot. The component structure and arrangement shall be explained in greater detail below. The detector arrangement 8 is held inside the line detector camera 4 so as to be adjustable in the direction of its longitudinal axis in the direction of the arrow 6. A detector arrangement 8 having two active detector elements forms the basis for the following discussion. This arrangement 8 represents only one of several possible embodiments within the scope of the invention. A diaphragm system 7, which contains the primary diaphragm, is held so as to be synchronously adjustable relative to the detector camera 4. The electromechanical connection of the line detector camera 4 with the diaphragm system is explained in greater detail with reference to FIG. 2.

Figure 2:
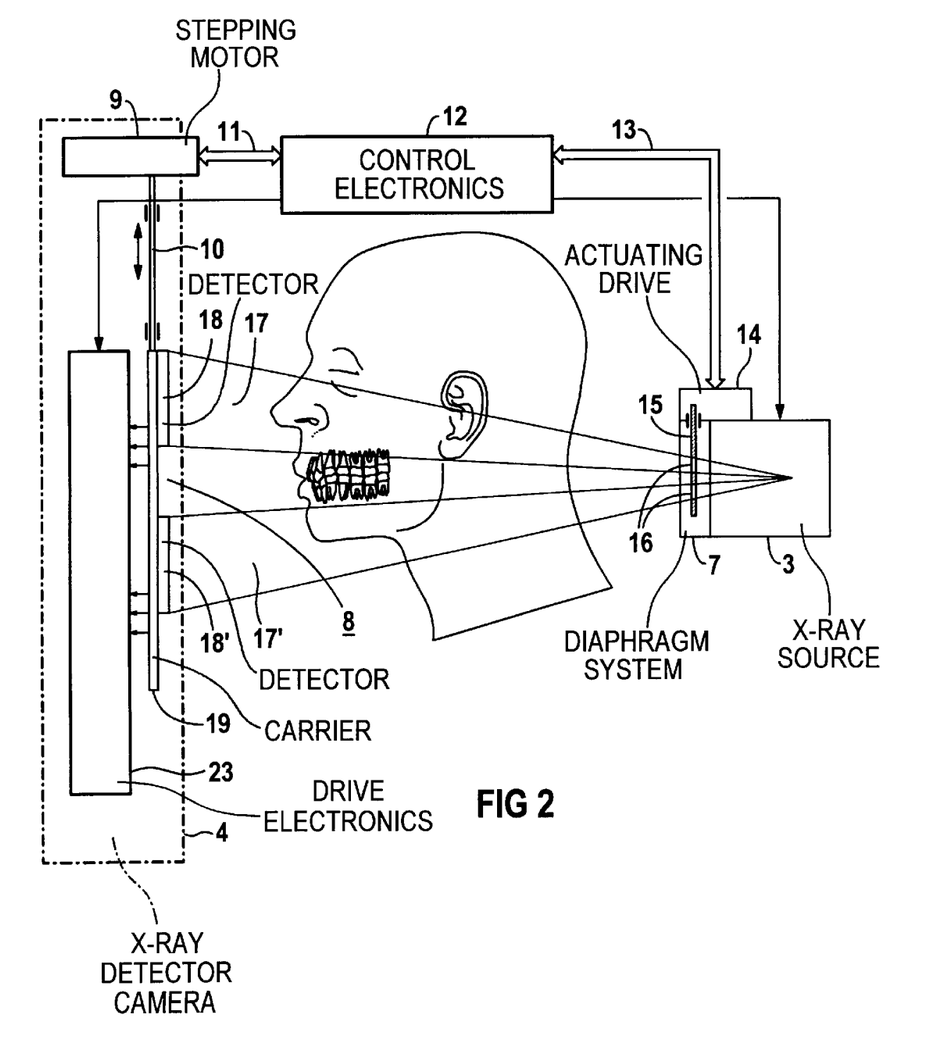
FIG. 2 is a schematic illustration for explaining the mechanical relationships of the apparatus components.

The detector elements (to be explained in greater detail below) arranged in the inside of the detector camera 4 can be adjusted along the principal detector axis with a suitable adjustment mechanism, such as with a stepping motor 9 and a spindle 10. Via a serial interface 11, the stepping motor 9 communicates with a control electronics 12 of the apparatus controller of the apparatus. Via a further interface 13, the control electronics 12 forwards control commands to an actuating drive 14 arranged at the X-ray source 3. The synchronous adjustment of a primary diaphragm 15 of the diaphragm system 7 ensues with this actuating drive 14. The primary diaphragm 15 contains two diaphragm apertures 16 arranged spaced from each other. The X-rays emitted by the radiation source 3 are thus divided into two ray beams 17, 17' that are focussed such that they exactly strike two detectors 18, 18' arranged in the inside of the line detector camera 4. The two detectors 18, 18' are arranged on a carrier 19 that, as described, is adjustable in the indicated arrow direction with the adjustment mechanism.

Figure 3:
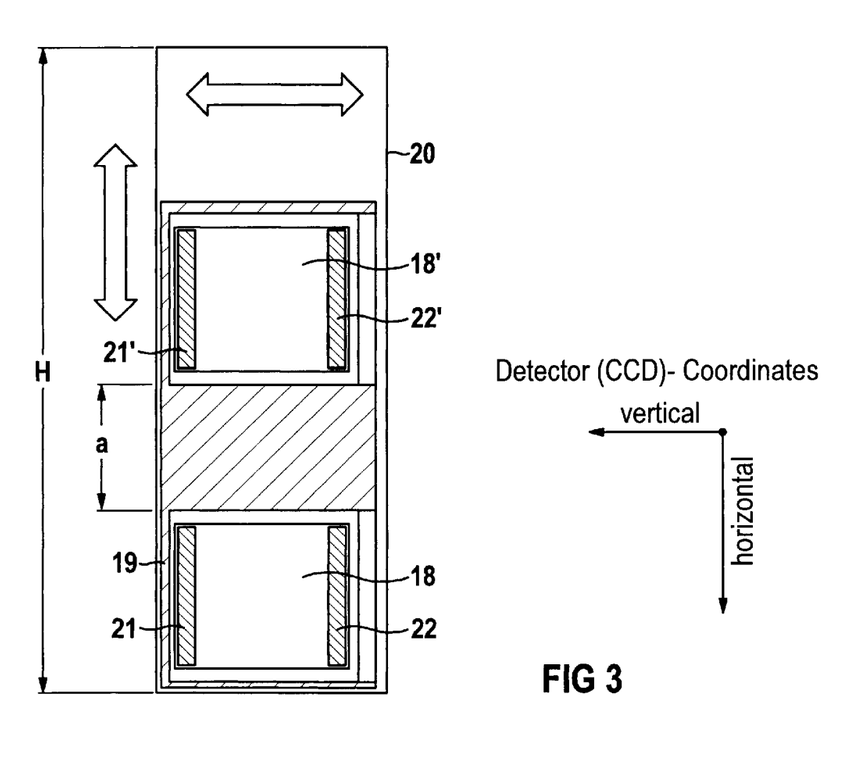
FIG. 3 shows a first embodiment of a detector arrangement used in the inventive apparatus.

FIG. 3 shows the detector arrangement in a front view. The carrier 19 on which the two detectors 18, 18' are secured is displaceably held in a frame Clock-out registers 21, 21' of the detectors, as can be seen from the coordinate reference at the right in FIG. 3, are fashioned as horizontal registers, i.e. in the TDI direction (TDI stands for Time Delay and Integration and is a term employed in CCD technology), which proceeds transversely relative to the displacement direction. Two readout registers 22, 22' in one embodiment must be provided when one wishes to implement the clocking-out in the opposite direction, i.e. when one wishes to make sub-exposures during the return phase of the rotary unit 2.

Drive electronics 23 is provided for the two detectors 18, 18'.

Figure 4:
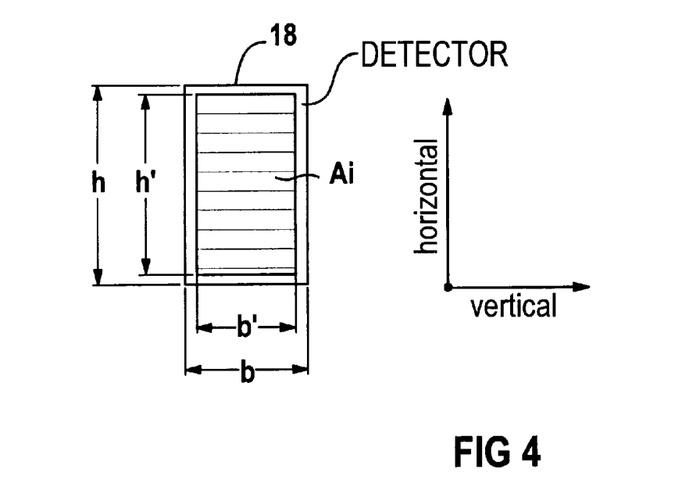
FIG. 4 shows a first embodiment of a detector arrangement useable in the method and apparatus of the invention.

FIG. 4 shows an individual detector 18 having the dimensions standard for intra-oral sensors. Such sensors typically have a height (h) of 30 mm and a width (b) of 20 mm. The sensor surface irradiated by radiation is referenced Ai and has a height (h') of 26 mm and a width (b') of 18 mm.

Figure 5:
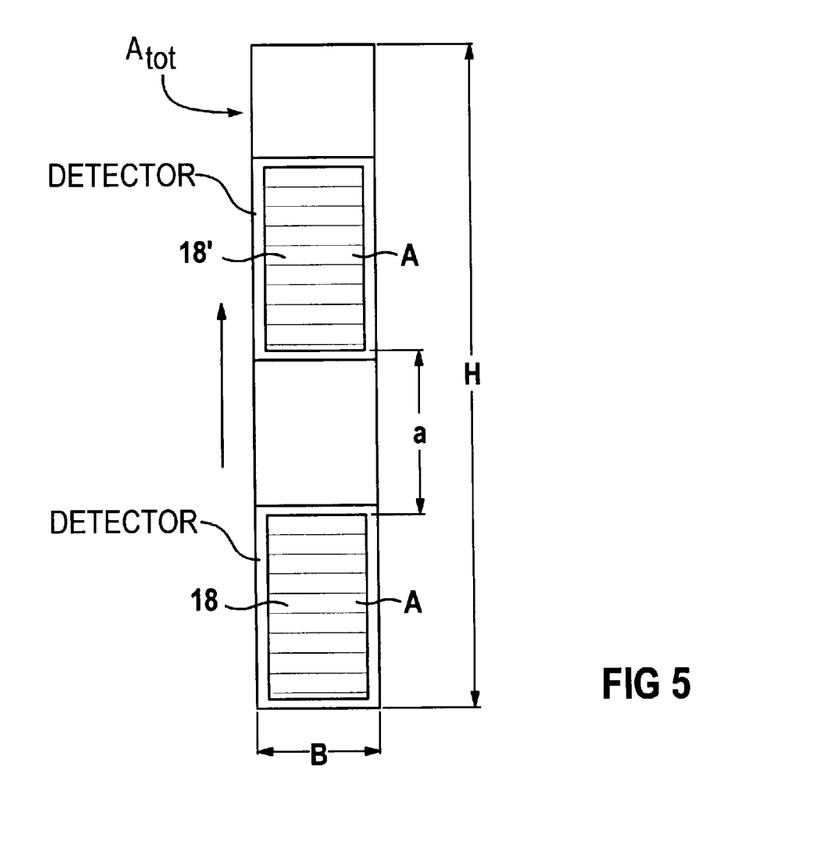
FIG. 5 shows a second embodiment of a detector arrangement useable in the method and apparatus of the invention.

FIG. 5 shows a detector arrangement having a number of detectors. The detector area ($A_{tot}$) required for the subject exposure is divided into n areas, the sub-area A corresponding to the nth part of the total detector area ($A_{tot}$). Each sub-area is composed of m sensor areas (Ai), with m representing the number of detectors employed. Two detectors 18, 18' are provided in this example. The irradiated sub-area A resulting from this arrangement amounts to 2×Ai. In relation thereto, the total detector area required for the exposure of a subject is referenced $A_{tot}$. Let it be assumed that this total area ($A_{tot}$) should amount to H×B=100 mm×20 mm. The two detectors 18, 18' are secured to the carrier 19 at the spacing (a) from one another, with the spacing (a) being dimensioned such that the irradiated sub-areas supplement one another to form a complete image without any deterioration being perceptible at the image transitions. In the arrangement shown as an example, the detector and the radiation fan beam are respectively shifted by approximately 25 mm in the arrow direction, i.e. along the longitudinal axis of the detectors. In order to achieve the indicated overall height of about 100 mm, accordingly, two exposure (image acquisition) phases are needed, a first in the illustrated basic position and a second wherein the two detectors are shifted by approximately 25 mm in the arrow direction.

Alternatively, an arrangement with only one detector can be provided.

Figure 9:
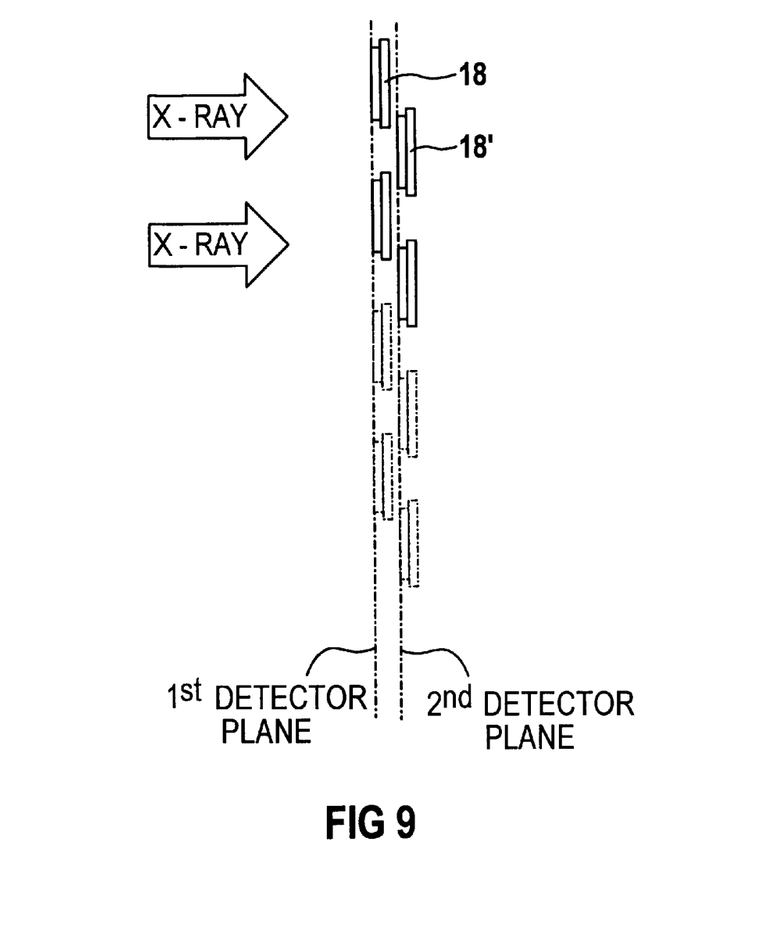
FIG. 9 shows a fourth embodiment of a detector arrangement useable in the method and apparatus of the invention.
Figure 10:
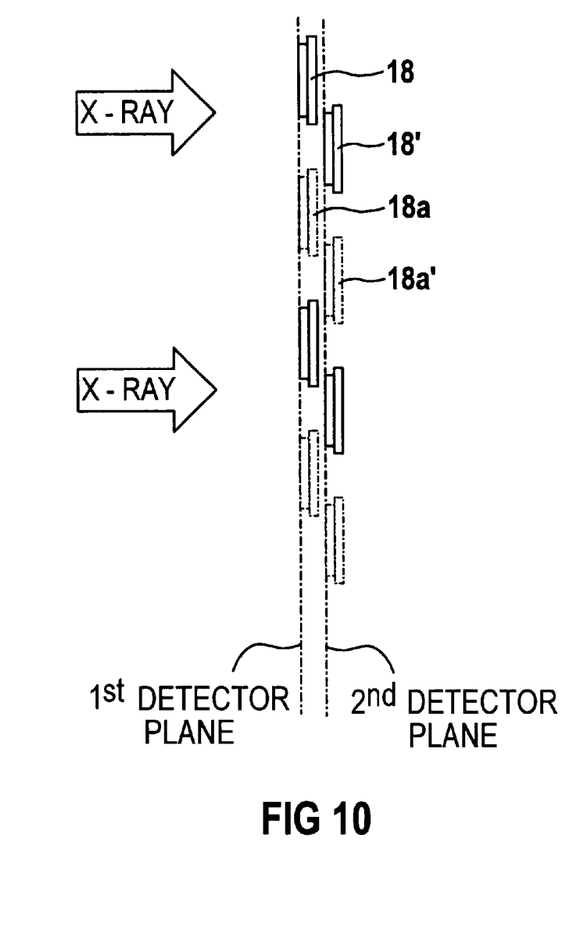
FIG. 10 shows a fifth embodiment of a detector arrangement useable in the method and apparatus of the invention.

In order to reduce the number of exposure phases, it is alternatively possible to partly or completely close the gaps (that have arisen due to the detectors being spaced with the distance (a)) with additional detectors. It is assumed that a mere joining of the detectors to one another in the prescribed image detector plane cannot be realized without influences that limit the image quality since inactive joint structures that do not contribute to the image acquisition arise at the abutting locations. In order to avoid these disadvantages, the gap is closed by detectors which are arranged in a second image detector plane farther from the x-ray source. FIGS. 9 and 10 show such an arrangement. Here, the detectors are arranged overlapping, so that a greater part of the line or the entire line can be irradiated in an exposure phase.

The advantage of this arrangement is a reduction in the number of exposure phases and the elimination of a complicated diaphragm control, since no sub-areas have to be blanked out. Since the costs per active detector area rise disproportionately with those of the detector area, the use of further, small detectors is an economical solution.

Occlusions which may be produced by detectors arranged in the first plane can be corrected with standard image processing techniques such as, for example, gain and artifact correction, insofar as these occlusions are produced by inactive detector structures.

In addition to being defined by other parameters, the slice to be resolved is defined by the position attitude of the image detector planes. When, as described, two or even more different detector planes are used for the acquisition of a slice, then this can negatively influence the desired slice resolution. It has been shown in practice that an offset of up to 3 mm does not require any compensatory measures. For compensation (when needed), the charges can be moved with different speeds in the detector. In TDI technology, the charges in the detectors of the second plane are moved faster with a higher TDI clock rate than the charge in those detectors that are arranged closer to the radiator. Analogous thereto, this compensation can also ensue in the "full frame mode".

In this case, four exposure phases with quadruple displacement of the detector respectively by about 25 mm are required.

Figure 6:
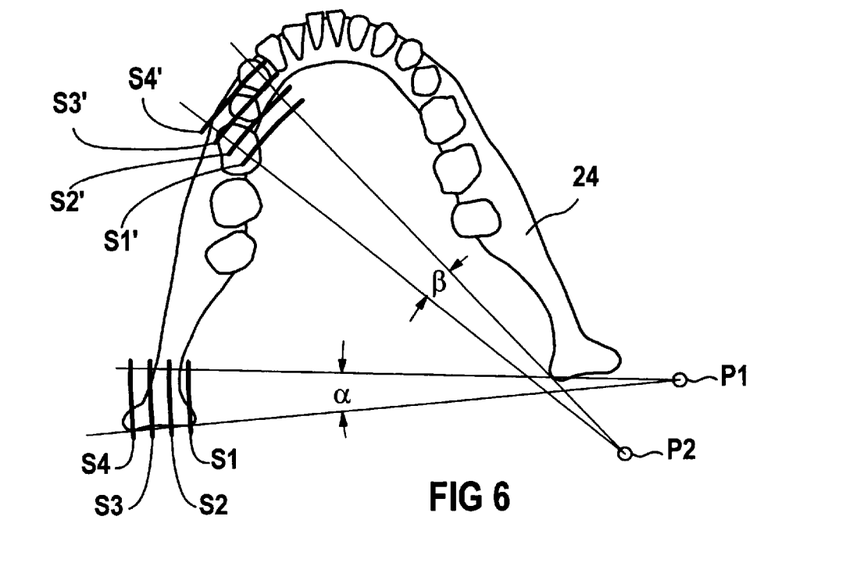
FIG. 6 is a schematic illustration for explaining transversal sections.

The executive sequence for achieving transversal slice exposures is explained in greater detail on the basis of FIG. 6. It is assumed that four transverse sections are to be recorded in the four indicated slice planes S1, S2, S3 and S4.

The operator first selects the exposure parameters (examined region, number, quality and size of the transverse sections as well as dose). These parameters can ensue at the apparatus itself or at a connected PC by selecting predefined programs, or can ensue by manual setting of the parameters. The exposure sequence is started after positioning the patient in the head retainer and positioning arrangement 5 (FIG. 1). The apparatus first adjusts itself by approaching reference points and subsequently positions itself in a start position for the following exposure series. The number of individual exposures is derived on the basis of the number of transversal slice exposures and the number of exposure phases. Let it be assumed in the exemplary embodiment of FIG. 6 that four different tomograms S1 through S4 of the left temperomaxillary joint and, subsequently, four more tomograms S1' through S4' of a further jaw section of the illustrated mandibular arch, are to be produced. The rotary unit 2 is first moved into the position P1, from which the X-ray source 3 can emit rays onto the desired imaging region that, for example, should film the illustrated angle α. The tomogram S1 is produced by, beginning from an initial position rotating the rotary unit 2 through the angle α. After the exposure for the slice position S1 has been produced, the X-ray source 3 is turned off and the rotary unit 2 is moved back by the swivel angle a into the initial position. Subsequently, the slice positions S2, S3 and S4 are produced in succession. Other slice positions for further subject portions can be analogously produced, for example proceeding from the position P2, as shown. The kinematic motion sequence of the rotary unit 2 carrying the X-ray source 2 and line detector camera 4 is known, as is the drive of the detectors according to the TDI method required in order to obtain the desired layer.

In this last-described exposure procedure, the actual exposure with radiation is implemented during forward running of the rotary unit 2. The radiation is turned off in the return phase or is rendered ineffective by a diaphragm adjustment.

There are a number of possibilities for acquiring the four slices in the exemplary embodiment. One way is to first completely produce one slice, i.e. initially implementing two exposure sequences with a detector displacement given (a detector arrangement with two detectors) and correspondingly registering the further slices S2, S3 and S4 thereafter.

Alternatively, there is the possibility of registering all four slices in one detector position, subsequently displacing the detector arrangement and in turn subsequently registering all four slices in the second detector position. This version has the advantage that further motion events are not needed, which may slow the overall executive sequence.

As already initially addressed, it can be advantageous to implement tomograms during the return run of the rotary unit 2. To that end, it is necessary to equip the detectors with a second readout register (positions 22, 22' in FIG. 3) in order to be able to also implement the TDI process in the opposite direction.

Figure 7:
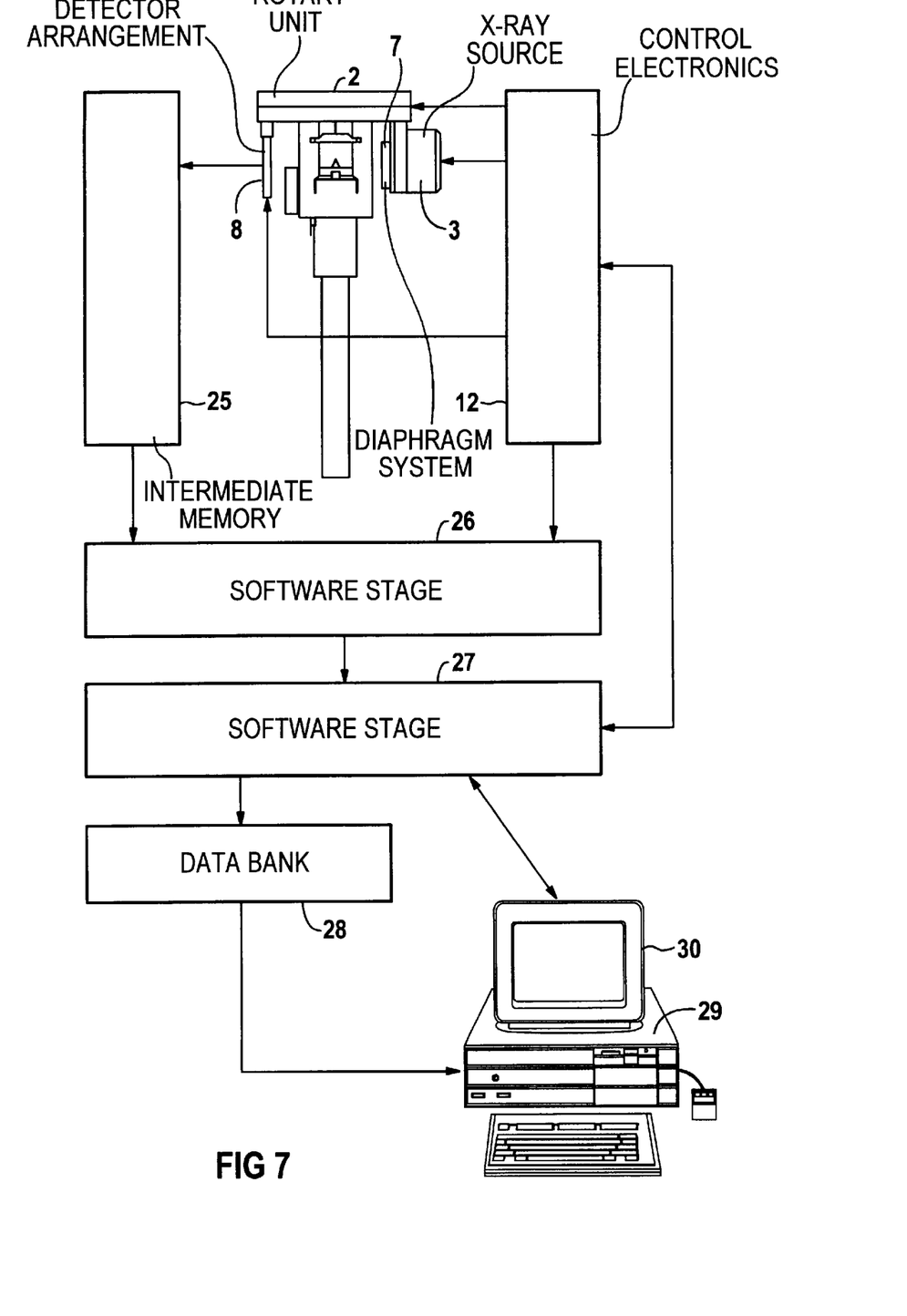
FIG. 7 is a block circuit diagram of the apparatus of the invention.

FIG. 7 shows a block circuit diagram of the inventive apparatus and illustrates the relationship between the individual components. The apparatus controller 12 generates control signals for the detector arrangement 8, the diaphragm system 7 and X-ray source 3 and coordinates the execution (the motion) of the detector arrangement 8 and of the X-ray source 3 for each sub-image sequence according to the predetermined path in an exposure. The image data acquired during a sequence are stored in an intermediate memory 25. The apparatus controller 12 not only controls the X-ray source 3, the diaphragm system 7 and the detector arrangement 8 but also supplies exposure related radiation, position and path data to a software stage 26. The software stage 26 also processes the image data of the sub-images stored in the intermediate memory 25 that had been acquired with the detectors to a form a "raw image". This "raw image" is subsequently processed in a further software stage 27 to form an X-ray image, which is subsequently stored in a data bank 28. From the data band 28, for example, the data (image) can be called via a PC and displayed on a monitor 30. Advantageously, the parameters necessary for an exposure can be generated by the PC 29 from the software stage 27, these being forwarded therefrom to the apparatus controller 12.

The summation or integration needed for producing the tomograms can—as shown—ensue with the assistance of the CCDs that are operated in the TDI mode. The image thereby arises during the data acquisition on the basis of an "analog" summation within the active CCD area.

Alternatively, the image acquisition is possible without the TDI method by acquiring an image of the complete sensor area and storing it for each motion increment according to the necessary sensor motion. The term "full frame mode" or "area mode" is usually employed for this operating mode. A more economical technology (for example, CMOS technology) can be used in this alternative instead of CCD technology. In this case, the summation of picture elements needed for the creation of a sharp slice ensues after the data acquisition in a correspondingly designed computer unit.

After intermediate storage, the signals of a sub-image generated in each exposure are processed into a tomogram by signal processing software. Each transversal exposure is thus compiled from the appertaining exposures by a computer, is processed and stored, and is then displayed on a picture screen. The geometrical positions during the exposure sequences, and the dimensions of the detector as well, are known to the computer during the compilation.

As initially mentioned, the detector width should be at least 20 mm in order to meet minimum demands made of the depth of field of the transversal slice to be resolved. The effective detector width can be enlarged, and thus the depth of field of the transversal slice can be improved, by transverse displacement of the aforementioned detector structures and by repeating the described exposure procedures.

A further exposure set arises with every transverse displacement. As described, these exposure sets can be produced with the "analog" TDI method or "digital" summation. These exposure sets must likewise be summed in order also to take the transverse displacement into consideration. Understandably, only the "digital" method can be meaningfully applied for the summation of the digitized exposure sets.

As already mentioned, the primary diaphragm adjustment ensues synchronously with the adjustment of the detectors. This can ensue with a motor-displaceable template in the way shown in FIG. 2. Alternatively, the diaphragm displacement can ensue by a corresponding adjustment of a lower and upper limitation; it is likewise possible to provide a rotatable diaphragm with diaphragm apertures situated at different locations.

Figure 8:
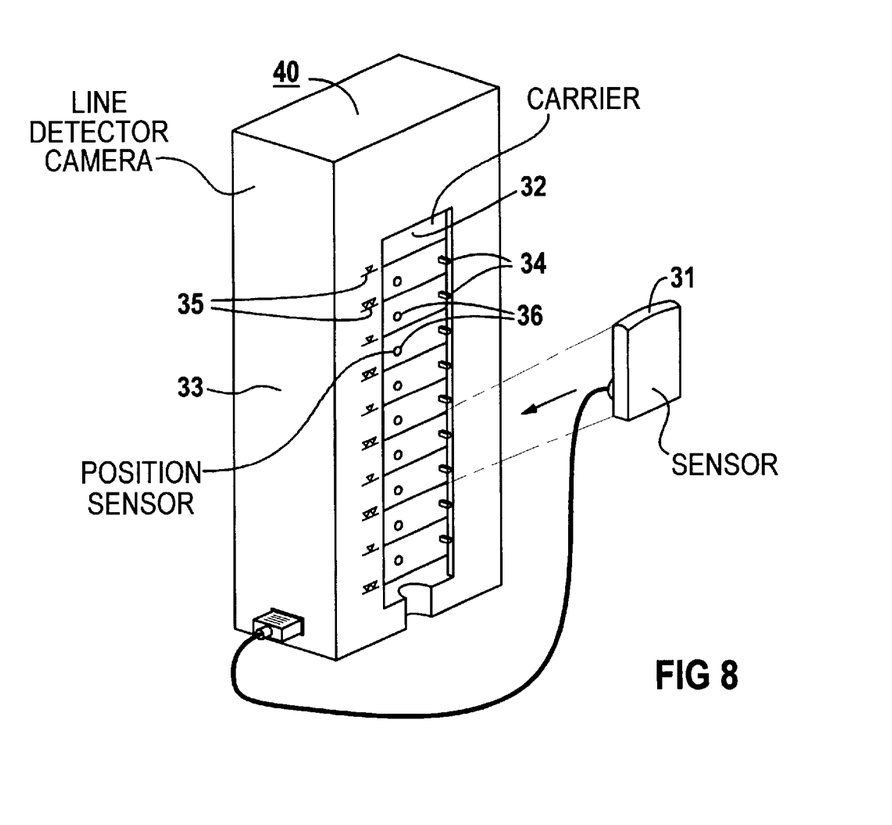
FIG. 8 shows a third embodiment of a detector arrangement useable in the method and apparatus of the invention.

FIG. 8 shows a version referred to as a "dual use" version wherein a complete intra-oral sensor 31 utilized in a known way for intra-oral exposures can also be utilized for producing transversal tomograms. To this end, a carrier 32 is provided that, like the carrier 19 of the above-described embodiment, is adjustably arranged in the housing 33 of the line detector camera 40. The carrier 32 contains a number of clamp elements or similar retainer elements that make it possible to hold the sensor 31 in different positions. To this end, the retainer elements 34 are arranged such that the sensor 31 can be selectively held dependent on the exposure type or exposure area. Symbol markings 35 applied to the housing 35 facilitate the selection of the exposure area or exposure type. Instead of symbols, for example, a metric scale can be provided as a marking. The position of the sensor 31 being utilized is acquired by position sensors 36. These can be of an electromechanical nature (microswitches or the like) or of an optoelectronic nature as well (light barriers or the like). The electrical linkage and control otherwise ensues as described.

Although various minor modifications might be suggested by those skilled in the art, it should be understood that our wish to embody within the scope of the patent warranted hereon all such modifications as reasonably and properly come with the scope of our contribution to the art.

We claim as our invention:

1. A method for producing x-ray exposures of a jaw region of a human subject, comprising the steps of:
    providing a detector arrangement having at least one detector with a total detector area required for an exposure composed of a plurality of sub-areas;
    in a first sub-exposure, irradiating one of said sub-areas of said detector with x-rays, limited by a diaphragm, emitted by an x-ray source, said x-rays passing through a subject and striking said one of said sub-areas; and
    following said first sub-exposure, conducting at least one further sub-exposure by shifting said detector arrangement through a shift along a selected axis thereof, and synchronously adjusting said diaphragm dependent on said shift so that said x-ray beam strikes a different one of said sub-areas of said detector, until said detector area has been irradiated by x-rays.

2. A method as claimed in claim 1 wherein the step of providing a detector arrangement comprises providing an image pick-up unit as said detector arrangement and acquiring a sequence of rapid exposures with said image pick-up unit, and integrating each exposure in a computer to produce an image of said total detector area.

3. A method as claimed in claim 2 wherein the step of providing an image pick-up unit comprises providing a CCD sensor and operating said CCD sensor in full frame operating mode.

4. A method as claimed in claim 1 wherein the step of shifting said detector arrangement comprises shifting said detector arrangement along a longitudinal axis and a transverse axis thereof.

5. A method as claimed in claim 1 comprising the additional steps of:
    mounting said x-ray source and said detector arrangement on a rotary unit and rotating said rotary unit around said subject for producing said first sub-exposure and said at least one further sub-exposure, said exposures being produced while rotating said rotary unit in at least one of a forward direction and a return direction.

6. A method as claimed in claim 5 wherein the step of displacing said detector arrangement comprises displacing said detector arrangement only when all sub-exposures for a predetermined detector position have been conducted for all exposures at said detector position.

7. A method as claimed in claim 1 wherein the step of providing a detector arrangement comprises providing a CCD sensor operated according to a TDI method as said detector arrangement.

8. An apparatus for producing x-ray exposures of body parts of a human subject, comprising:
    an x-ray source which emits an x-ray beam, and having a diaphragm arrangement which limits said x-ray beam;
    a radiation detector arrangement comprising a plurality m of detectors and having a total detector area, said total detector area comprising n sub-areas; and
    means for positioning said diaphragm arrangement and said detector arrangement for conducting a plurality of sub-exposures with said x-ray beam, in each sub-exposure, striking only one of said sub-areas, and for re-positioning said diaphragm arrangement and said detector arrangement in subsequent sub-exposures, following said first sub-exposure, until said total detector area is irradiated by x-rays from said x-ray beam.

9. An apparatus as claimed in claim 8 further comprising means for operating said x-ray source for producing respective contributions to a plurality of tomograms, said plurality of tomograms being respectively at different distances from said x-ray source, in each of said sub-exposures.

10. An apparatus as claimed in claim 8 wherein said detector arrangement comprises at least one detector having dimensions corresponding to an intra-oral sensor.

11. An apparatus as claimed in claim 10 wherein said detector arrangement comprises a single detector displaceably held in a frame.

12. An apparatus as claimed in claim 10 wherein said detector arrangement comprises a plurality of detectors disposed spaced from each other and each having an irradiated detector height, with a spacing between any two adjacent detectors being less than or equal to said irradiated detector height.

13. An apparatus as claimed in claim 10 wherein said detector arrangement comprises a readout register for integrating an output of said detector arrangement in switchable integration directions.

14. An apparatus as claimed in claim 8 wherein said detector arrangement comprises at least one detector having dimensions corresponding to an intra-oral sensor, and further comprising a carrier having a plurality of retainer elements for holding said at least one sensor in respectively different positions, said carrier having a plurality of position sensors respectively associated with said different positions, each position sensor supplying a signal to said means for positioning when the position associated with the position sensor is occupied by said at least one detector.

15. An apparatus as claimed in claim 14 wherein said carrier further comprises a plurality of visible markings respectively identifying said positions.

16. An apparatus as claimed in claim 15 wherein said detector arrangement comprises a first set of detectors disposed in a first plane at a first distance from said x-ray source, said detectors in said first set being spaced from each other with gaps respectively between neighboring detectors in said first set of detectors, and a second set of detectors disposed in a second plane at a second distance from said radiator, said detectors in said second set being disposed at respective locations coinciding with said gaps between the detectors in said first set of detectors.

17. An apparatus as claimed in claim 16 wherein said first and second sets of detectors form a line-shape detector arrangement, and said line-shape detector arrangement further comprising first and second detectors respectively disposed at opposite ends of said line-shape detector arrangement.

18. An apparatus as claimed in claim 16 further comprising means for respectively separately integrating signals from each of said first and second sets of detectors.

19. An apparatus as claimed in claim 8 wherein said detector arrangement comprises a plurality of pairs of neighboring detectors, the detectors in each pair of neighboring detectors overlapping each other.

* * * * *